United States Patent [19]

Holtkamp, Sr.

[11] Patent Number: Plant 6,575

[45] Date of Patent: Jan. 31, 1989

[54] AFRICAN VIOLET PLANT NAMED ANNIE

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 21,786

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Annie characterized by its generally single, bright red-purple flowers which are wavy, particularly at the edges; strong, upright flower stems that curve toward the center to form a bouquet above the leaves, profuse and continuous flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Annie.

The new cultivar was referred to during the breeding and selection process by the designation H 40/1, and is a product of a planned breeding program. The new cultivar was originated from a cross made by me in the controlled breeding program in Isselburg, Federal Republic of Germany. The female, or seed parent, was a cultivar designated 349 Apple Blossom. The male, or pollen parent, was a cultivar designated B 15/8 Red Purple.

Annie was discovered and selected by me in 1982 as a flowering plant within the progeny of the stated cross in a controlled environment in Isselburg, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Annie has not been observed under all possible environmental conditions. The phenotype may vary significantly with variations in environment such as temperature, light intensity and day length. The following observations, measurements and values describe the new cultivar as grown in Haffen, Federal Republic of Germany and Nashville, Tenn., under greenhouse conditions which closely approximate those generally used in commercial practice.

The following traits have been repeatedly observed and are determined to be basic characteristics of Annie which in combination distinguish this African violet as a new and distinct cultivar:

(1) Strong, upright flower stems carry bright red-purple flowers having wavy edges.

(2) In the first flash of flowers, a tight bouquet is formed above the leaves.

(3) Profuse and continuous flowering, with two flower stems being generated at each leaf axil.

(4) Each stem carries up to 8 and more upright flower stems each of which carry 7 to 10 and more single flowers.

(5) Vigorous grower.

(6) Plant saleable 9–10 weeks after potting.

(7) Long-lasting, non-dropping flowers.

The accompanying color photographic drawing shows a typical specimen plant of the new cultivar. The colors appearing in the photograph are as true as possible with color illustration of this type.

In the following description, color references are made to The Royal Horticultural Society Color Chart (RHS), except where general colors of ordinary significance are referred to. Color values were taken under natural sunlight at approximately 1:00 p.m. in Nashville, Tenn.

Botanical classification: *Saintpaulia ionantha,* Ramat., cv. Annie.

Parentage:

*Male parent.*—B 15/8 Red Purple.

*Female parent.*—349 Apple Blossom.

Propagation: The new cultivar holds its distinguishing characteristics through successive propagations by leaf cuttings.

Plant: From 6 cm to 8 cm tall when grown in pots, and approximately 22–25 cm in diameter when fully grown.

*Leaves.*—General form: Round. Diameter: 60–70 mm. Texture: Velvet. Aspect: Shiny, slightly hairy. Veins: Well pronounced, light green. Color (upper side): Yellow green 147A. Color (under side): Yellow green 148D. Petiole: Brownish-green.

*Flowers.*—Buds: Round to bell-shaped, 7–8 mm before opening, purplish. Sepals: Five, spear-shaped, hairy. Color: Dark green. Calyx: Shape: Funnel-shaped. Aspect: Spear-shaped, hairy. Peduncle: Character: Strong, upright, hairy. Color: Brown.

*Individual flowers.*—Size: Approximately 45 mm. Shape: Generally violet-shaped but wavy, particularly at edge. Surface appears crystal-like. Color (upper side): 73D. Color (under side): 73D. Borne: Each flower stem carries 9 and more flowers on strong, upright peduncles, with the compact bouquet extending above the leaves. Most flowers are single, although occasionally an additional petal is added, giving a semi-double appearance. Flowering habit: Flowers 8–9 weeks after potting, with substantially continuous flowering thereafter.

*Reproductive organs.*—Stamens: 2 and occasionally 3 where the additional petal is added. Anthers: 2 with four cells. Filaments: 5 mm, yellowish green. Pollen Color: Yellow 7a. Styles: 6–8 mm, slightly purple, bent.

*Roots.*—Well established, white, turning slightly brownish when older.

Disease resistance: Good.

General observations: Annie is a vigorous grower, with attractive medium to dark green velvet, slightly shiny leaves. Approximately 9–10 weeks after potting the plant has developed 9–12 strong upright flower stems which carry 9 and more single flowers. The flowers are bright red-purple with wavy edges and are carried on strong peduncles which form a compact flower head that is freestanding above the leaves. The continuous production of new flower stems makes Annie a so-called semperflorence. With previously known violets there is one flower stem out of each leaf axil; Annie is generating 2 out of each leaf axil, thereby producing continuous flowering characteristics under optimal light conditions.

I claim:

1. A new and distinct cultivar of African violet named Annie, as described and illustrated, and particularly characterized by its generally single, bright red-purple flowers which are wavy, particularly at the edges; strong, upright flower stems that curve toward the center to form a bouquet above the leaves, profuse and continuous flowering, vigorous growth habit, flowering 9–10 weeks after potting, and its long-lasting and non-dropping flowers.

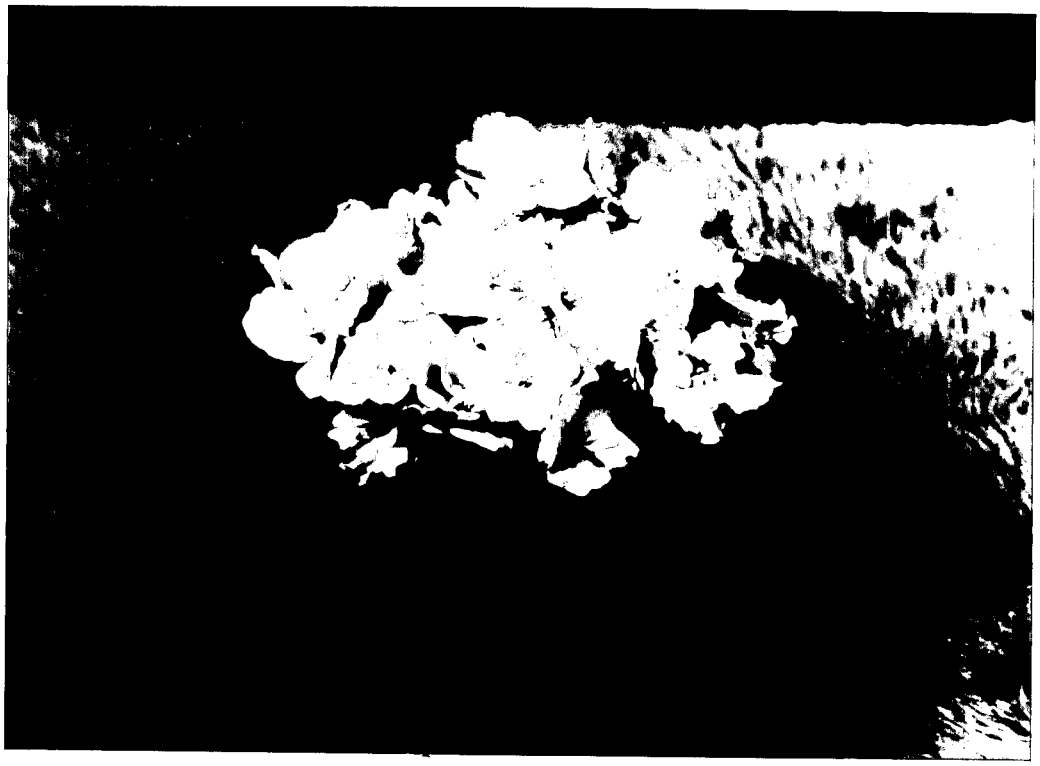

* * * * *